US00PP24717P2

(12) United States Plant Patent
Koppe

(10) Patent No.: US PP24,717 P2
(45) Date of Patent: Jul. 29, 2014

(54) *BEGONIA* PLANT NAMED 'KRBELIN02'

(50) Latin Name: *Begonia hybrida*
Varietal Denomination: KRBELIN02

(75) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 46 days.

(21) Appl. No.: 13/573,168

(22) Filed: Aug. 27, 2012

(51) Int. Cl.
*A01H 5/00* (2006.01)

(52) U.S. Cl.
USPC ..... Plt./343

(58) Field of Classification Search
USPC ..... Plt./343
See application file for complete search history.

*Primary Examiner* — Annette Para
(74) *Attorney, Agent, or Firm* — C. A. Whealy

(57) ABSTRACT

A new and distinct cultivar of *Begonia* plant named 'KRBELIN02', characterized by its compact, upright, outwardly spreading and mounded plant habit; freely basal branching habit; shiny dark red and dark purple to black-colored leaves; and excellent postproduction longevity.

2 Drawing Sheets

Botanical designation: *Begonia hybrida.*
Cultivar denomination: 'KRBELIN02'.

BACKGROUND OF THE INVENTION

The present invention relates to a new and distinct cultivar of *Begonia* plant, botanically known as *Begonia hybrida* and hereinafter referred to by the name 'KRBELIN02'.

The new *Begonia* plant is a product of a planned breeding program conducted by the Inventor in Ermelo, The Netherlands. The objective of the breeding program is to create new compact *Begonia* plants with unique and attractive leaf coloration.

The new *Begonia* plant originated from a cross-pollination made by the Inventor in Ermelo, The Netherlands in January, 2008 of a proprietary selection of *Begonia hybrida* identified as code number 99BREX-31, not patented, as the female, or seed, parent with a proprietary selection of *Begonia hybrida* identified as code number KV03B265-08, not patented, as the male, or pollen, parent. The new *Begonia* plant was discovered and selected by the Inventor as a single flowering plant from within the progeny of the stated cross-pollination in a controlled greenhouse environment in Ermelo, The Netherlands in January, 2009.

Asexual reproduction of the new *Begonia* plant by leaf cuttings taken in a controlled greenhouse environment in Ermelo, The Netherlands since February, 2009 has shown that the unique features of this new *Begonia* plant are stable and reproduced true to type in successive generations.

SUMMARY OF THE INVENTION

Plants of the new *Begonia* have not been observed under all possible environmental conditions and cultural conditions. The phenotype may vary somewhat with variations in environmental conditions such as temperature and light intensity, without, however, any variance in genotype.

The following traits have been repeatedly observed and are determined to be the unique characteristics of 'KRBELIN02'. These characteristics in combination distinguish 'KRBELIN02' as a new and distinct *Begonia* plant:

1. Compact, upright, outwardly spreading and mounded plant habit.
2. Freely basal branching habit.
3. Shiny dark red and dark purple to black-colored leaves.
4. Excellent postproduction longevity.

Plants of the new *Begonia* differ primarily from plants of the female parent selection in leaf color as plants of the female parent selection have red-colored leaves with black-colored venation. In addition, plants of the new *Begonia* are more compact than plants of the female parent selection.

Plants of the new *Begonia* differ primarily from plants of the male parent selection in leaf color stability as plants of the male parent selection have leaves with unstable color patterns whereas plants of the new *Begonia* have leaves with stable color patterns.

Plants of the new *Begonia* can be compared to plants of *Begonia hybrida* 'Inca Fire', not patented. In side-by-side comparisons conducted in Ermelo, The Netherlands, plants of the new *Begonia* differed primarily from plants of 'Inca Fire' in leaf color as plants of 'Inca Fire' had greyed purple-colored leaves.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical plant of 'KRBELIN02' grown in a container.

The photograph on the second sheet is a close up view of the upper and lower surfaces of typical leaves of 'KRBELIN02'.

DETAILED BOTANICAL DESCRIPTION

The aforementioned photographs and following observations and measurements describe plants grown during the spring in 13-cm containers in a glass-covered greenhouse in Ermelo, The Netherlands and under cultural practices typical of commercial *Begonia* production. During the production of the plants, day temperatures averaged 20° C. and night temperatures averaged 18° C. Plants were twelve weeks old when the photographs and description were taken. In the following description, color references are made to The Royal Horticultural Society Colour Chart, 2007 Edition, except where general terms of ordinary dictionary significance are used.

Botanical classification: *Begonia hybrida* 'KRBELIN02'.

Parentage:

*Female, or seed, parent*.—Proprietary selection of *Begonia hybrida* identified as code number 99BREX-31, not patented.

*Male, or pollen, parent*.—Proprietary selection of *Begonia hybrida* identified as code number KV03B265-08, not patented.

Propagation:

*Type*.—By leaf cuttings.

*Time to develop roots*.—About 20 days at temperatures of 20° C.

*Time to produce a rooted young plant*.—About nine weeks at temperatures of 20° C.

*Root description*.—Fine, fibrous; white to orange brown in color.

*Rooting habit*.—Freely branching; medium density; plants of the new *Begonia* have not been observed to form tubers.

Plant description:

*Plant habit and form*.—Compact, upright, outwardly spreading and mounded plant habit; overall plant shape roughly globular.

*Growth habit*.—Moderately vigorous growth habit and moderate growth rate; suitable for 12-cm and larger containers; under optimal environmental and cultural conditions, usually about twelve weeks are required to produce proportional 13-cm potted plants from cuttings.

*Branching habit*.—Freely basal branching habit, about 16 basal branches develop per plant; dense and bushy habit.

*Plant height*.—About 25.4 cm.

*Plant width*.—About 41.8 cm.

*Leaves*.—Arrangement: Alternate; simple. Length: About 14.5 cm. Width: About 9.1 cm. Shape: Ovate to broadly ovate. Apex: Acute. Base: Oblique. Margin: Biserrate, laciniate; undulate. Texture, upper surface: Smooth, glabrous; velvety. Texture, lower surface: Smooth; slightly velvety; sparsely pubescent along veins. Luster, upper surface: Glossy. Luster, lower surface: Dull. Venation pattern: Palmate. Color: Developing leaves, upper surface: Center, close to 59A; towards the margins, close to 203A. Developing leaves, lower surface: Center, close to N186C; towards the margins, close to N186A. Fully expanded leaves, upper surface: Center, more intense than 46A; towards the margins, between N186A and 203A; venation, between N186C and 203A. Fully expanded leaves, lower surface: Center, close to 183A to 183B; towards the margins, close to 187A; venation, close to 187A. Petioles: Length: About 12.5 cm. Diameter: About 4 mm. Texture, upper and lower surfaces: Moderately pubescent. Color, upper and lower surfaces: Between N186C and 187A. Lenticels: Present on petioles. Length: About 5 mm. Width: About 0.3 mm. Color: Close to N155C. Stipules: One present at the base of the leaf. Length: About 1.2 cm. Width: About 9 mm. Shape: Ovate with acute to mucronulate apex and cuneate base. Color: Close to 45A.

Flower description: Flower development has not been observed on plants of the new *Begonia*. The new *Begonia* was selected on the basis of its unique foliage characteristics and its lack of flowers.

Postproduction longevity: Plants of the new *Begonia* have excellent postproduction longevity and have been observed to last at least six weeks under interior environmental conditions.

Disease & pest resistance: Resistance to pathogens and pests common to *Begonia* has not been observed on plants of the new *Begonia*.

Temperature tolerance: Plants of the new *Begonia* have been observed to tolerate high temperatures of about 35° C. and to be hardy to USDA Hardiness Zone 10.

It is claimed:

1. A new and distinct *Begonia* plant named 'KRBELIN02' as illustrated and described.

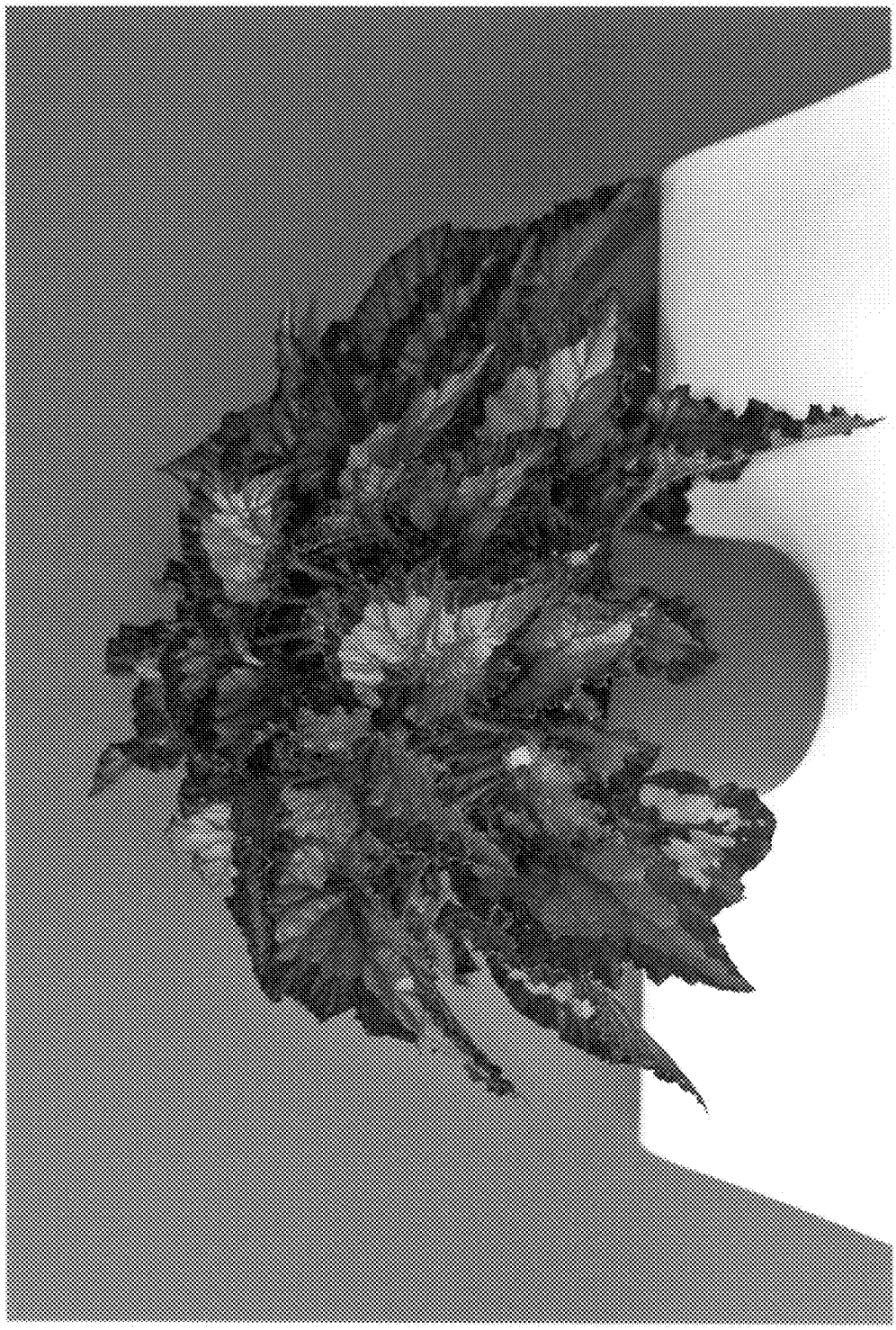

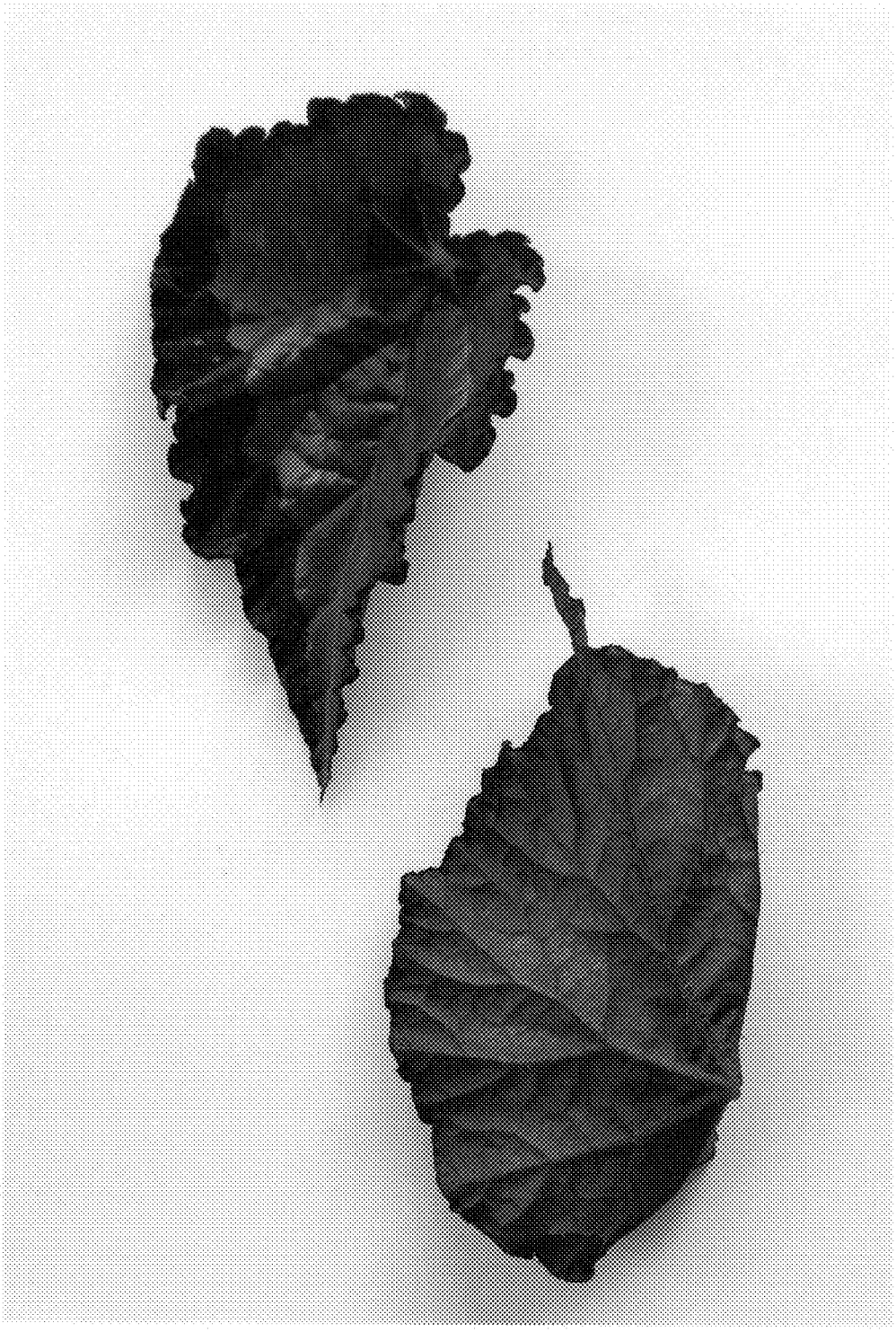

* * * * *